United States Patent
Stoller et al.

(10) Patent No.: US 9,102,718 B2
(45) Date of Patent: Aug. 11, 2015

(54) ANTI-S1P ANTIBODY TREATMENT OF PATIENTS WITH OCULAR DISEASE

(75) Inventors: Glenn L. Stoller, Roslyn, NY (US);
Marina Safonov, Escondido, CA (US);
Scott R. Pancoast, San Diego, CA (US);
James Leigh Hsu, San Diego, CA (US)

(73) Assignee: Lpath, Inc., San Diego, CA (US)

( * ) Notice: Subject to any disclaimer, the term of this patent is extended or adjusted under 35 U.S.C. 154(b) by 0 days.

(21) Appl. No.: 13/695,287

(22) PCT Filed: Apr. 29, 2011

(86) PCT No.: PCT/US2011/034561
§ 371 (c)(1),
(2), (4) Date: Oct. 30, 2012

(87) PCT Pub. No.: WO2011/137344
PCT Pub. Date: Nov. 3, 2011

(65) Prior Publication Data
US 2013/0058951 A1 Mar. 7, 2013

Related U.S. Application Data

(60) Provisional application No. 61/330,276, filed on Apr. 30, 2010.

(51) Int. Cl.
*A61K 39/395* (2006.01)
*C07K 16/18* (2006.01)
*C07K 16/22* (2006.01)
*A61K 39/00* (2006.01)

(52) U.S. Cl.
CPC .............. *C07K 16/18* (2013.01); *C07K 16/22* (2013.01); *A61K 2039/505* (2013.01); *A61K 2039/507* (2013.01); *C07K 2317/73* (2013.01); *C07K 2317/76* (2013.01)

(58) Field of Classification Search
CPC ............... C07K 16/22; C07K 2317/73; C07K 2317/76; A61K 39/395; A61K 39/39533
See application file for complete search history.

(56) References Cited

U.S. PATENT DOCUMENTS

| | | | |
|---|---|---|---|
| 7,829,674 B2 * | 11/2010 | Sabbadini et al. | 530/387.1 |
| 8,026,342 B2 | 9/2011 | Sabbadini et al. | |
| 8,444,970 B2 * | 5/2013 | Sabbadini et al. | 424/130.1 |
| 8,614,103 B2 * | 12/2013 | Sabbadini et al. | 436/547 |
| 2007/0148168 A1 | 6/2007 | Sabbadini et al. | |
| 2008/0213274 A1 | 9/2008 | Sabbadini et al. | |
| 2009/0074789 A1 | 3/2009 | Sabbadini et al. | |
| 2010/0034814 A1 | 2/2010 | Sabbadini et al. | |
| 2010/0098700 A1 | 4/2010 | Sabbadini et al. | |

FOREIGN PATENT DOCUMENTS

WO 2009/124294 A2 10/2009

OTHER PUBLICATIONS

Bashshur et al., Am. J. Ophthamol., 2008, 249-256, 145(2).
Brown et al., N. Eng. J. Med., 2006, 1432-1444, 355(14).
Bylsma et al., Clin. Exp. Optom., 2005, 322-334, 88(5).
Caballero et al., Exp. Eye Res., 2009, 367-377, 88(3).
Chae et al., J. Clin. Invest., 2004, 1082-1089, 114(8).
Ciulla et al., Curr. Opin. Ophthalmol., 2001, 442-449, 12(6).
Dart, Eye, 2003, 886-892, 17(8).
Eichler et al., Med. Res. Rev., 1995, 481-496, 15(6) (Abstract Only).
Gryziewicz, Adv. Drug Deliv. Rev., 2005, 2092-2098, 57(14).
Heier et al., Ophthalmology, 2006, 633-642e4, 113(4).
Kono et al., Amer. J. Resp. Cell & Molecular. Biol., 2007, 395-404, 37(4).
La Cour et al., Drugs Aging, 2002, 101-133, 19(2).
Lai et al., J. Immunol., 2008, 4323-4329, 180(6).
Lai et al., J. Immunol., 2008, 8010-8017, 181(11).
Lee et al., Biochem. Biophys. Res. Commun., 1999, 743-750, 264(3).
Liu et al., J. Clin. Invest., 2000, 951-961, 106(8).
Liu et al., Curr. Opin. Ophthalmol., 2004, 221-226, 15(3).
Maier et al., Klin. Monbl. Augenheilkd, 2008, 818-824, 225(9) (Abstract Only).
Maines et al., Invest. Ophthalmol., 2006, 5022-5031, 47.
Pauleikhoff, Retina, 2005, 1065-1084, 25(8).
Rosenfeld et al., N. Eng. J. Med., 2006, 1419-1431, 355(14).
Rotstein et al., J. Lipid Res., 2010, 1247-1262, 51(6).
Skoura, A. J. Clin. Invest., 2007, 2506-2516, 117(9).
Spaide, Am. J. Ophthalmol., 2006, 149-156, 141(1).
Su et al., J. Biol. Chem., 1994, 16512-16517, 269.
Sun et al., J. Mol. Cell. Cardiol., 1996, 851-858, 28(5).
Sun et al., Cardiovasc. Res., 2000, 250-256, 46(2).
Swaney, Exp. Eye Res., 2008, 367-375, 87(4).
Tezel et al., Mol. Med., 2004, 417-420, 10(9).
Ueno et al., J. Cell. Physiol., 2008, 13-22, 217(1).
Van Wijngaarden et al., JAMA, 2005, 1509-1513, 293(12).
Visentin et al., Cancer Cell, 2006, 225-238, 9(3).
Wang et al., Microvasc. Res., 2009, 39-45, 77(1).
Willett et al., Nat. Med., 2004, 145-147, 10(2).
Xie, J. Cell. Physiol., 2009, 192-198, 218(1).
US NIH, Safety Study of iSONEP, 2008, printed Aug. 22, 2013 (5 pages).

* cited by examiner

*Primary Examiner* — Robert Landsman
(74) *Attorney, Agent, or Firm* — Acuity Law Group, P.C.; Daniel M. Chambers

(57) ABSTRACT

The present invention relates to methods that involve administration of an anti-S1 P antibody or antibody fragment or derivative to a subject having or suspected of having an ocular disease or condition, including one involving choroidal neovascularization, in order to achieve a desired effect. Such effects include reducing the size of a choroidal neovascularization lesion in the eye, decreasing or resolving retinal pigment epithelial detachment, decreasing central retinal lesion thickness, and preserving or improving visual acuity. Pharmaceutical compositions comprising an anti-S1 P antibody for ocular administration are also provided. The compositions and methods are particularly useful for treating subjects having age-related macular degeneration, particularly exudative or wet age-related macular degeneration.

11 Claims, 4 Drawing Sheets

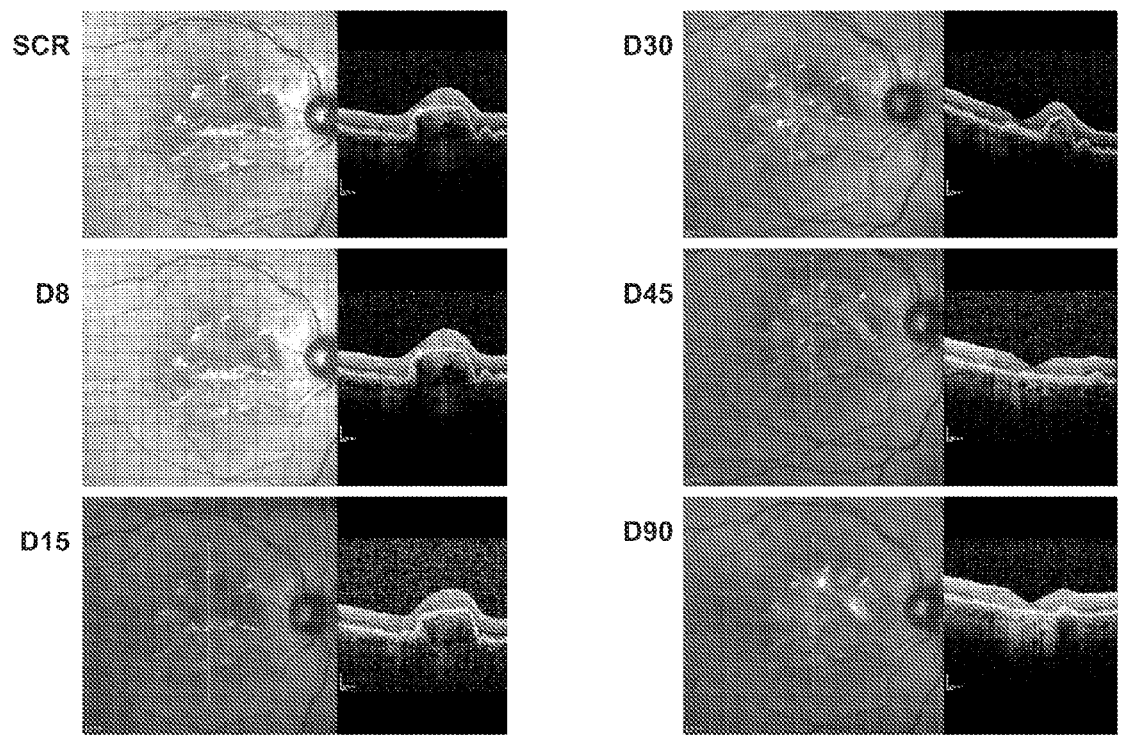
Figure 2A – Fundus photographs and OCT, Subject 2, 0.2 mg ISONEP

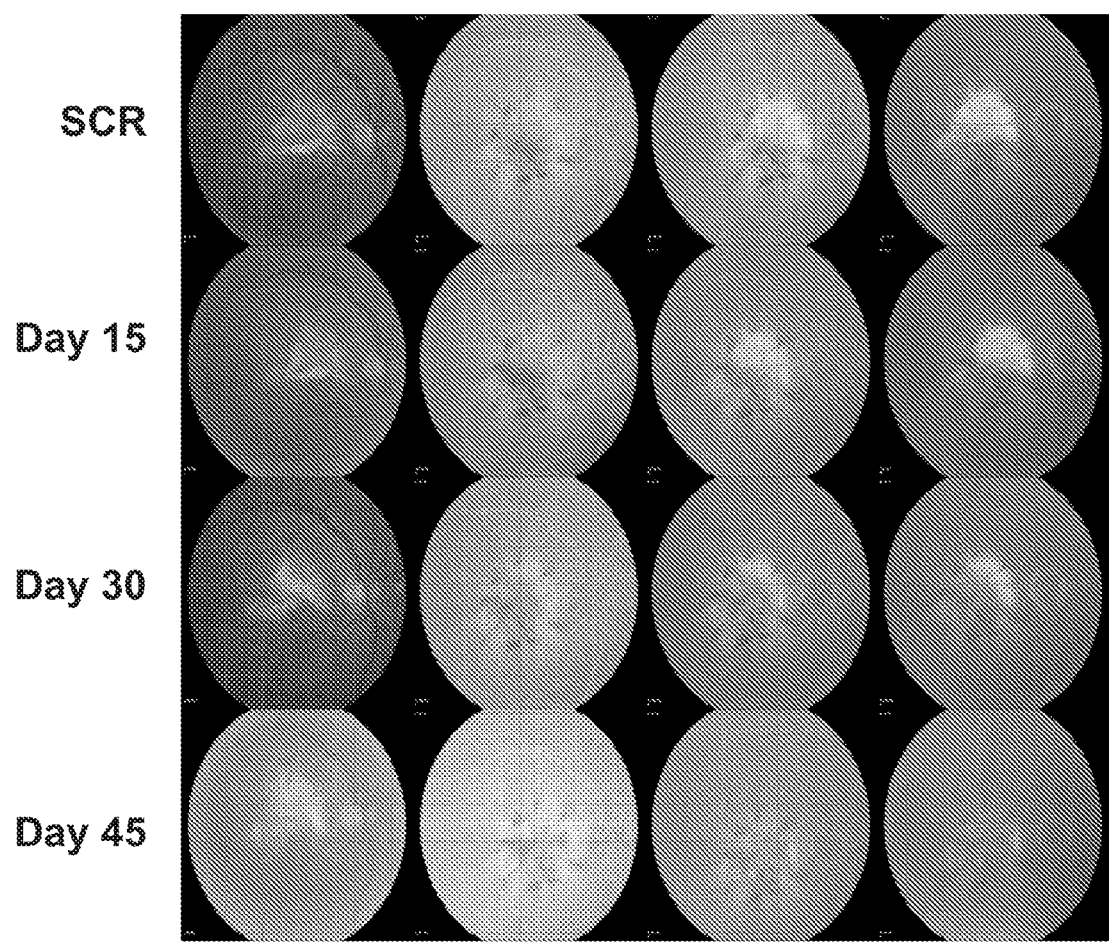
Figure 2B- FA, Subject 2, 0.2 mg ISONEP

Figure 3- SDOCT, Subject 15, 1.8 mg ISONEP
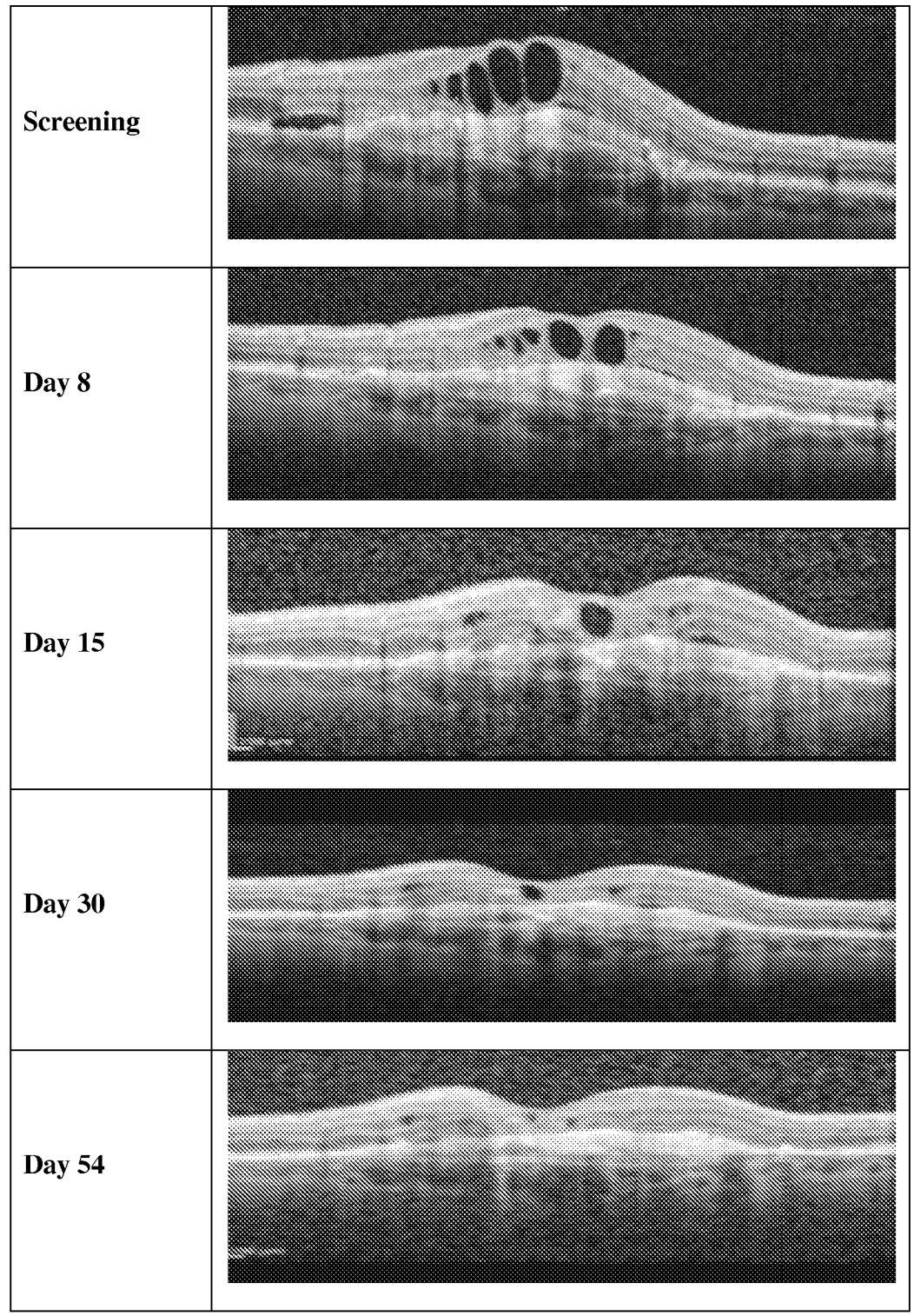

ANTI-S1P ANTIBODY TREATMENT OF PATIENTS WITH OCULAR DISEASE

RELATED APPLICATION

This application claims the benefit of and priority to U.S. provisional patent application Ser. No. 61/330,276, filed 30 Apr. 2010, the contents of which are hereby incorporated by reference for any and all purposes.

SEQUENCE LISTING

The instant application contains a Sequence Listing that has been submitted via EFS-Web and is hereby incorporated by reference in its entirety. Said ASCII copy, created on Apr. 22, 2011, is named LPT3013US.txt, and is 13,628 bytes in size.

TECHNICAL FIELD

The present invention relates to methods of treatment for ocular disorders using antibodies, including humanized antibodies, to sphingosine-1-phosphate (S1P), as well as to anti-S1P antibody fragments and derivatives. Such antibodies can be successfully used in the treatment of ocular diseases or conditions, including age-related macular degeneration (AMD), choroidal neovascularization (CNV), and retinal pigment epithelium (RPE) detachment (also called retinal pigment epithelial detachment or PED).

SEQUENCE LISTING

The instant application contains a Sequence Listing submitted via the Electronic Filing Sytem on Apr. 29, 2011 and, is hereby incorporated by reference in its entirety. Said ASCII copy, created on Apr. 20, 2011, is named LPT3013PC.txt, and is 13,628 bytes in size.

BACKGROUND OF THE INVENTION

I. Introduction

The following description includes information that may be useful in understanding the present invention. It is not an admission that any such information is prior art, or relevant, to the presently claimed inventions, or that any publication specifically or implicitly referenced is prior art or even particularly relevant to the presently claimed invention.

II. Background

The present invention relates to methods of decreasing or attenuating aberrant neovascularization, angiogenesis, aberrant fibrogenesis, fibrosis and scarring, and inflammation and immune responses. These processes, separately or together are involved in many diseases and conditions. These diseases or conditions may be systemic or may be relatively localized, for example to the skin or to the eye.

A. Ocular Diseases and Conditions

Pathologic or aberrant angiogenesis/neovascularization, aberrant remodeling, fibrosis and scarring and inflammation occur in association with retinal and ocular ischemic diseases such as age-related macular degeneration (AMD), diabetic retinopathy (DR) and in retinopathy of prematurity (ROP) and other developmental disorders [Eichler et al. (2006), Curr Pharm Des, vol 12: 2645-60] as well as being a result of infections and mechanical injury to the eye [Ciulla et al. (2001), Curr Opin Ophthalmol, vol 12: 442-9 and Dart et al (2003), Eye, vol 17: 886-92].

Pathologic ocular angiogenesis is a leading cause of blindness in a variety of clinical conditions. Choroidal neovascularization (CNV) occurs in a number of ocular diseases, the most prevalent of which is the exudative or "wet" form of AMD. As a result of an increasingly aged population, AMD is a modern day epidemic and the leading cause of blindness in the western world in patients over age 60. Despite the epidemic of vision loss caused by AMD, only a few therapies, mostly anti-VEGF based, can slow the progression of AMD and even fewer can reverse vision loss [Bylsma and Guymer (2005), Clin Exp Optom., vol 88: 322-34, Gryziewicz (2005), Adv Drug Deliv Rev, vol 57: 2092-8 and Liu and Regillo (2004), Curr Opin Ophthalmol, vol 15: 221-6.]. Therefore, discovering new treatments for pathologic neovascularization is extremely important.

AMD is used here for illustrative purposes in describing ocular conditions relating to aberrant angiogenesis/neovascularization, aberrant remodeling, fibrosis and scarring, and inflammation, which conditions are found in other ocular diseases and disorders as disclosed and claimed herein. AMD involves age-related pathologic changes [Tezel, Bora and Kaplan (2004), Trends Mol Med, vol 10: 417-20 and Zarbin (2004), Arch Ophthalmol, 122: 598-614]. Multiple hypotheses exist but the exact etiology and pathogenesis of AMD are still not well understood. Aging is associated with cumulative oxidative injury, thickening of Bruch's membrane and drusen formation. Oxidative stress results in injury to retinal pigment epithelial (RPE) cells and, in some cases, the choriocapillaris [Zarbin (2004), Arch Ophthalmol, vol 122: 598-614 and Gorin et al. (1999), Mol Vis., vol 5: 29]. Injury to RPE likely elicits a chronic inflammatory response within Bruchs membrane and the choroid [Johnson et al. (2000), Exp Eye Res., vol 70: 441-9]. This injury and inflammation fosters and potentiates retinal damage by stimulating CNV and atrophy [Zarbin (2004), Arch Ophthalmol, vol 122: 598-614 and Witmer et al. (2003), Prog Retin Eye Res, vol 22:1-29]. CNV results in defective and leaky blood vessels (BV) that are likely to be recognized as a wound [Kent and Sheridan (2003), Mol Vis, vol 9: 747-55]. Wound healing arises from the choroid and invades the subretinal space through Bruchs membrane and the RPE. Wound healing responses are characterized by a typical early inflammation response, a prominent angiogenic response and tissue formation followed by end-stage maturation of all involved elements. Wound remodeling may irreversibly compromise photoreceptors and RPEs thereby, justifying the need to treat CNV with more than anti-angiogenic therapies [La Cour, Kiilgaard and Nissen (2002), Drugs Aging, vol 19: 101-33.12].

Alterations in the normal retinal and sub-retinal architecture as a result of CNV related fibrosis, edema and inflammation individually or cumulatively, leads to AMD related visual loss [Tezel and Kaplan (2004), Trends Mol Med, vol 10: 417-20 and Ambati et al. (2003), Sury Ophthalmol, vol 48: 257-93]. The multiple cellular and cytokine interactions which are associated with exudative AMD greatly complicate the search for effective treatments. While CNV and edema are manageable in part by anti-VEGF therapeutics, potential treatments to mitigate scar formation and inflammation have not been adequately addressed [Bylsma and Guymer (2005), Clin Exp Optom, vol 88: 322-34 and Pauleikhoff (2005), Retina, vol 25: 1065-84]. As long as the neovascular complex remains intact, as appears to be the case in patients treated with anti-VEGF agents, the potential for subretinal fibrosis and future vision loss persists.

In some patients with AMD or conditions such as polypoidal choroidal vasculopathy (PCV), the retinal pigmented epithelium (RPE) may detach. This detachment is often referred to as pigment epithelial detachment (PED), and it may occur for example, in disorders such as AMD and PCV that disrupt the normal junction between the basement membrane of the RPE and the inner collagenous layer of Bruch's membrane. When the detachment affects the macula, vision is affected. Polypoidal choroidal vasculopathy (PCV) is characterized by abnormal development of blood vessels in the deeper layers of the eye; whether PCV is a sub-type of AMD or a separate disorder remains unclear.

Anti-VEGF-A therapies represent a recent, significant advance in the treatment of exudative AMD. However, the phase III VISION Trial with PEGAPTANIB, a high affinity aptamer that selectively inhibits the 165 isoform of VEGF-A, demonstrated that the average patient continues to lose vision and only a small percent gained vision [Gragoudas et al. (2004), N Engl J Med, vol 351: 2805-16] Inhibition of all isoforms of VEGF-A (pan-VEGF inhibition) with the antibody fragment ranibizumab (LUCENTIS®, Genentech) yielded much more impressive results [Brown et al., N Eng Med, 2006 355:1432-44, Rosenfeld et al. N Eng J Med 2006355:1419-31]. The 2-year MARINA trial and the 1 year ANCHOR trial demonstrated that approximately 40% of patients achieve some visual gain. Although these results represent a major advance in our ability to treat exudative AMD, they also demonstrate that 60% of patients do not have visual improvement. Furthermore, these patients had to meet strictly defined inclusion and exclusion criteria. The results in a larger patient population may be less robust. The market leaders in treatment of wet AMD are LUCENTIS® (ranibizumab) and off-label use of AVASTIN® (bevacizumab, a humanized monoclonal antibody against VEGF-A).

There is still a well-defined need to develop further therapeutic agents that target other steps in the development of CNV and the processes that ultimately lead to photoreceptor destruction. First, the growth of choroidal BVs involves an orchestrated interaction among many mediators, not just VEGF, offering an opportunity to modulate or inhibit the entire process [Gragoudas et al. (2004), N Engl J Med, vol 351: 2805-16]. Second, exudative AMD is comprised of vascular and extravascular components. The vascular component involves vascular endothelial cells (EC), EC precursors and pericytes. The extravascular component, which volumetrically appears to be the largest component, is composed of inflammatory, glial and retinal pigment epithelium (RPE) cells and fibroblasts. Tissue damage can result from either component. These other aspects of the pathologic process are not addressed by current anti-VEGF treatments. Targeting additional elements of the angiogenic cascade associated with AMD could provide a more effective and synergistic approach to therapy [Spaide R F (2006), Am J Ophthalmol, vol 141: 149-156].

1. Inflammation in Ocular Disease

There is increasing evidence that inflammation, specifically macrophages and the complement system [Klein et al. (2005), Science, vol 308: 385-9 and Hageman et al. (2005), Proc Natl Acad Sci USA, vol 102: 7227-32] play an important role in the pathogenesis of AMD, both the dry or atrophic form which accounts for 85-90% of AMD cases, and the wet form of AMD characterized by the growth of abnormal blood vessels. Dry macular degeneration is diagnosed when yellowish spots known as drusen begin to accumulate from deposits or debris from deteriorating tissue primarily in the area of the macula. Gradual central vision loss may occur. There is no effective treatment for the atrophic (dry) form of AMD. Atrophic AMD is triggered by abnormalities in the retinal pigment epithelium (RPE) that lies beneath the photoreceptor cells and normally provides critical metabolic support to these light-sensing cells. Secondary to RPE dysfunction, macular rods and cones degenerate leading to the irreversible loss of vision. Oxidative stress, ischemia, formation of drusen, accumulation of lipofuscin, local inflammation and reactive gliosis represent the pathologic processes implicated in pathogenesis of atrophic AMD. Of these processes, inflammation is emerging as a key contributor to tissue damage. Macrophage infiltration into the macula of patients with dry AMD has been demonstrated to be an important component of the damaging inflammatory response.

In exudative AMD, histopathology of surgically excised choroidal neovascular membranes demonstrates that macrophages are almost universally present [Grossniklaus, et al. (1994), Ophthalmology, vol 101: 1099-111 and Grossniklaus et al. (2002), Mol Vis, vol 8: 119-26]. There is mounting evidence that macrophages may play an active role in mediating CNV formation and propagation [Grossniklaus et al. (2003), Mol Vis, vol 8: 119-26; Espinosa-Heidmann, et al. (2003), Invest Ophthalmol Vis Sci, vol 44: 3586-92; Oh et al. (1999), Invest Ophthalmol Vis Sci, vol 40: 1891-8; Cousins et al. (2004), Arch Ophthalmol, vol 122: 1013-8; Forrester (2003), Nat Med, vol 9: 1350-1 and Tsutsumi et al. (2003), J Leukoc Biol, vol 74: 25-32] by multiple effects which include secretion of enzymes that can damage cells and degrade Bruchs membrane as well as release pro-angiogenic cytokines [Otani et al. (1999), Ophthalmol Vis Sci, vol 40: 1912-20 and Amin, Puklin and Frank (1994), Invest Ophthalmol Vis Sci, vol 35: 3178-88] At the site of injury, macrophages exhibit micro-morphological signs of activation, such as degranulation [Oh et al. (1999), Invest Ophthalmol Vis Sci, vol 40: 1891-8 and Trautmann et al. (2000), J Pathol, vol 190: 100-6]. Thus it is believed that a molecule which limited macrophage infiltration into to the choroidal neovascular complex may help limit CNV formation.

2. Choroidal Neovascularization and Blood Vessel Maturation in Ocular Disease

Angiogenesis is an essential component of normal wound healing as it delivers oxygen and nutrients to inflammatory cells and assists in debris removal [Lingen (2001), Arch Pathol Lab Med, vol 125: 67-71]. Progressive angiogenesis is composed of two distinct processes: Stage I: Migration of vascular ECs, in response to nearby stimuli, to the tips of the capillaries where they proliferate and form luminal structures; and Stage II: Pruning of the vessel network and optimization of the vasculature [Guo et al. (2003), Am J Pathol, vol 162: 1083-93].

Stage I: Neovascularization. Angiogenesis most often aids wound healing. However, new vessels when uncontrolled, are commonly defective and promote leakage, hemorrhaging and inflammation. Diminishing dysfunctional and leaky BVs, by targeting pro-angiogenic GFs, has demonstrated some ability to slow the progression of AMD [Pauleikhoff (2005), Retina, vol 25: 1065-84.14 and van Wijngaarden, Coster and Williams (2005), JAMA, vol 293: 1509-13].

Stage II: Blood vessel maturation and drug desensitization. Pan-VEGF inhibition appears to exert its beneficial effect mostly via an anti-permeability action resulting in resolution of intra- and sub-retinal edema, as the actual CNV lesion does not markedly involute [Presentation. at Angiogenesis 2006 Meeting. 2006. Bascom Palmer Eye Institute Miami, Fla.]. The lack of marked CNV involution may in part be a result of maturation of the newly formed vessels due to pericyte coverage. Pericytes play a critical role in the development and maintenance of vascular tissue. The presence of pericytes seems to confer a resistance to anti-VEGF agents and compromise their ability to inhibit angiogenesis [Bergers and Song (2005), Neuro-oncol, vol 7: 452-64; Yamagishi and Imaizumi (2005), Int J Tissue React, vol 27: 125-35; Armulik, Abramsson and Betsholtz (2005), Circ Res, vol 97: 512-23; Ishibashi et al. (1995), Arch Ophthalmol, vol 113: 227-31]. An agent that has an inhibitory effect on pericyte recruitment would likely disrupt vascular channel assembly and the maturation of the choroidal neovascular channels thereby perpetuating their sensitivity to anti-angiogenic agents.

Remodeling of the vascular network involves adjustments in BV density to meet nutritional needs [Gariano and Gardner (2005), Nature, 438: 960-6]. Periods of BV immaturity corresponds to a period in which new vessels are functioning but have not yet acquired a pericyte coating [Benjamin, Hemo and Keshet (1998), Development, 125: 1591-8 and Gerhardt and Betsholtz (2003), Cell Tissue Res, 2003. 314: 15-23]. This delay is essential in providing a window of plasticity for the fine-tuning of the developing vasculature according to the nutritional needs of the retina or choroid.

The bioactive lipid sphingosine-1-phosphate (S1P), VEGF, PDGF, angiopoietins (Ang) and other growth factors (GF) augment blood vessel growth and recruit smooth muscle cells (SMC) and pericytes to naive vessels which promote the remodeling of emerging vessels [Allende and Proia (2002), Biochim Biophys Acta, vol 582: 222-7; Gariano and Gardner (2005), Nature, vol 438: 960-6; Grosskreutz et al. (1999), Microvasc Res, vol 58: 128-36; Nishishita, and Lin (2004), J Cell Biochem, vol 91: 584-93 and Erber et al. (2004), FASEB J, vol 18: 338-40.32]. Pericytes, most likely generated by in situ differentiation of mesenchymal precursors at the time of EC sprouting or from the migration and dedifferentiation of arterial smooth muscle cells, intimately associate and ensheath ECs resulting in overall vascular maturity and survival [Benjamin, Hemo and Keshet (1998), Development, vol 125: 1591-8]. Recent studies have demonstrated that S1P, and the S1P1 receptor, are involved in cell-surface trafficking and activation of the cell-cell adhesion molecule N-cadherin [Paik et al. (2004), Genes Dev, vol 18: 2392-403]. N-cadherin is essential for interactions between EC, pericytes and mural cells that promote the development of a stable vascular bed [Gerhardt and Betsholtz (2003), Cell Tissue Res, vol 314: 15-23]. Global deletion of the S1P1 gene results in aberrant mural cell ensheathment of nascent BVs required for BV stabilization during embryonic development [Allende and Proia (2002), Biochim Biophys Acta, vol 1582: 222-7]. Local injection of siRNA to S1P1 suppresses vascular stabilization in tumor xenograft models [Chae et al. (2004), J Clin Invest, vol 114: 1082-9]. Transgenic mouse studies have demonstrated that VEGF and PDGF-B promote the maturation and stabilization of new BVs [Guo et al. (2003), Am J Pathol, 162: 1083-93 and Gariano and Gardner (2005), Nature, vol 438: 960-6.50]. VEGF up-regulates Ang-1 (mRNA and protein) [Asahara et al. (1998), Circ Res, vol 83: 233-40]. Ang-1 plays a major role in recruiting and sustaining peri-endothelial support by pericytes [Asahara et al. (1998), Circ Res, vol 83: 233-40]. Intraocular injection of VEGF accelerated pericyte coverage of the EC plexus [Benjamin, Hemo and Keshet (1998), Development, vol 125: 1591-8]. PDGF-B deficient mouse embryos lack micro-vascular pericytes, which leads to edema, micro-aneurisms and lethal hemorrhages [Lindahl et al. (1997), Science, vol 277: 242-5]. Murine pre-natal studies have demonstrated that additional signals are required for complete VEGF- and PDGF-stimulation of vascular bed maturation. Based upon the trans-activation of S1P noted above, this factor could be S1P [Erber et al. (2004), FASEB J, vol 18: 338-40]. Vessel stabilization and maturation is associated with a loss of plasticity and the absence of regression to VEGF and other GF withdrawal and resistance to anti-angiogenic therapies [Erber et al. (2004), FASEB J, vol 18: 338-40 and Hughes. and Chan-Ling (2004), Invest Ophthalmol Vis Sci, vol 45: 2795-806]. Resistance of BVs to angiogenic inhibitors is conferred by pericytes that initially stabilize matured vessels and those that are recruited to immature vessels upon therapy [Erber et al. (2004), FASEB J, vol 18: 338-40]. After ensheathment of the immature ECs, the pericytes express compensatory survival factors (Ang-1 and PDGF-B) that protect ECs from pro-apoptotic agents.

3. Edema and Vascular Permeability

CNV membranes are composed of fenestrated vascular ECs that tend to leak their intravascular contents into the surrounding space resulting in subretinal hemorrhage, exudates and fluid accumulation [Gerhardt and Betsholtz (2003), Cell Tissue Res, vol 14: 15-23]. For many years the CNV tissue itself, and more recently intra-retinal neovascularization, have been implicated as being responsible for the decrease in visual acuity associated with AMD. It is now thought however, that macular edema caused by an increase in vascular permeability (VP) and subsequent breakdown of the blood retinal barrier (BRB), plays a major role in vision loss associated with AMD and other ocular diseases [Hughes and Chan-Ling (2004), Invest Ophthalmol Vis Sci, vol 45: 2795-806; Felinski and Antonetti (2005), Curr Eye Res, vol 30: 949-57; Joussen et al. (2003), FASEB J, vol 17: 76-8 and Strom et al. (2005), Invest Ophthalmol Vis Sci, vol 46: 3855-8].

4. Fibrosis, Fibrogenesis and Scar Formation

The formation of subretinal fibrosis leads to irreversible damage to the photoreceptors and permanent vision loss. As long as the neovascular complex remains intact, as appears to be the case in patients treated with anti-VEGF agents, the potential for subretinal fibrosis and future vision loss persists. In an update of the PRONTO study of RANIBIZUMAB, it was discovered that those patients who lost vision did so as a result of either subretinal fibrosis or a RPE tear [Presentation. at Angiogenesis 2006 Meeting. 2006. Bascom Palmer Eye Institute Miami, Fla.]. An agent that could diminish the degree of fibroblast infiltration and collagen deposition would likely be of value.

Fibroblasts, particularly myofibroblasts, are key cellular elements in scar formation in response to cellular injury and inflammation [Tomasek et al. (2002), Nat Rev Mol Cell Biol, vol 3: 349-63 and Virag and Murry (2003), Am J Pathol, vol 163: 2433-40]. Collagen gene expression by myofibroblasts is a hallmark of remodeling and necessary for scar formation [Sun and Weber (2000), Cardiovasc Res, vol 46: 250-6 and Sun and Weber (1996), J Mol Cell Cardiol, vol 28: 851-8]. S1P promotes wound healing by activating fibroblast migration and proliferation while increasing collagen production [Sun et al. (1994), J Biol Chem, vol 269: 16512-7]. S1P produced locally by damaged cells could be responsible for the maladaptive wound healing associated with remodeling and scar formation. Thus it is believed that S1P inhibitors are useful in diseases or conditions characterized, at least in part, by aberrant fibrogenesis or fibrosis. Herein, "fibrogenesis" is defined as excessive activity or number of fibroblasts, and "fibrosis" is defined as excessive activity or number of fibroblasts that leads to excessive or inappropriate collagen production and scarring, destruction of the physiological tissue structure and/or inappropriate contraction of the matrix leading to such pathologies as retinal detachment or other processes leading to impairment of organ function.

The role of bioactive lipids, particularly S1P, in disease, including ocular disease, and anti-S1P antibodies, are described in detail in commonly owned U.S. Pat. No. 7,829,674, U.S. patent application Ser. No. 12/258,353, now issued as U.S. Pat. No. 7,956,173; commonly owned and co-pending U.S. patent application Ser. No. 12/258,383, now issued as U.S. Pat. No. 8,026,342; and commonly owned and co-pending U.S. patent application Ser. No. 11/925,173, now issued as U.S. Pat. No. 8,614,103. Anti-S1P antibody formulations are described in commonly owned and co-pending U.S. patent application Ser. No. 12/418,597. This application incorporates by reference for all purposes all of the aforementioned applications, each in its entirety.

SUMMARY OF THE INVENTION

The invention provides methods that involve administration of an anti-S1P antibody or antibody fragment or derivative to a subject to achieve a desired effect. Such effects include reducing the size of a choroidal neovascularization lesion in the eye, decreasing or resolving retinal pigment epithelial detachment, decreasing retinal thickness and preserving, and/or improving visual acuity, all in subjects having or suspected of having choroidal neovascularization, particularly subjects having age-related macular degeneration, particularly exudative or wet age-related macular degeneration.

Thus, in one aspect, the invention concerns methods to treat or prevent an ocular disease or condition correlated with S1P in a subject known or suspected to have such a disease or condition in one or both eyes. An "an ocular disease or condition correlated with S1P" refers to any ocular disease or condition associated with a pathological role for S1P. These include ocular diseases, disorders, and conditions that involve pathologic or aberrant angiogenesis/neovascularization, aberrant remodeling, fibrosis and scarring and inflammation, including retinal and ocular ischemic diseases such as age-related macular degeneration (AMD), diabetic retinopathy (DR), retinopathy of prematurity (ROP), and polypoidal choroidal vasculopathy (PCV). The methods of the invention can be used to treat or prevent, for example, choroidal neovascularization lesions, including those that result from occult and/or minimally classic choroidal neovascularization, retinal pigment epithelial detachments, and central retinal thickening. In preferred embodiments, the methods of the invention can lead to or result in cessation of disease or symptom progression, as well as in reduction or resolution of symptoms such as choroidal neovascularization lesions, retinal pigment epithelial detachments, and central retinal thickening.

Pharmaceutical compositions comprising an anti-S1P antibody for ocular administration are also provided.

These and other aspects and embodiments of the invention are discussed in greater detail in the sections that follow.

BRIEF DESCRIPTION OF THE DRAWINGS

This patent application contains at least one figure executed in color. Copies of this patent application with color drawing(s) will be provided upon request and payment of the necessary fee.

FIG. 2A is a series of photographs showing fundus (left portion of each image—gray background) and OCT images (right side of each image—black background) from a patient with occult CNV. The subretinal edema and PED can be seen in the OCT images to diminish over time after ISONEP treatment.

FIG. 2B shows a series of FA images. The top row of images is from screening prior to ISONEP treatment, and subsequent rows are from days 15, 30 and 45 after treatment. Each individual image from left to right represents individual time points after dye (fluorescein) injection. By day 45 the lesion was determined to have regressed completely.

FIG. 3 shows a series of OCT images from a patient with minimally classic CNV. This patient had intraretinal edema (dark bubbles near center of each image) that can be seen to resolve completely over time after ISONEP treatment.

DETAILED DESCRIPTION OF THE INVENTION

Figure 1:
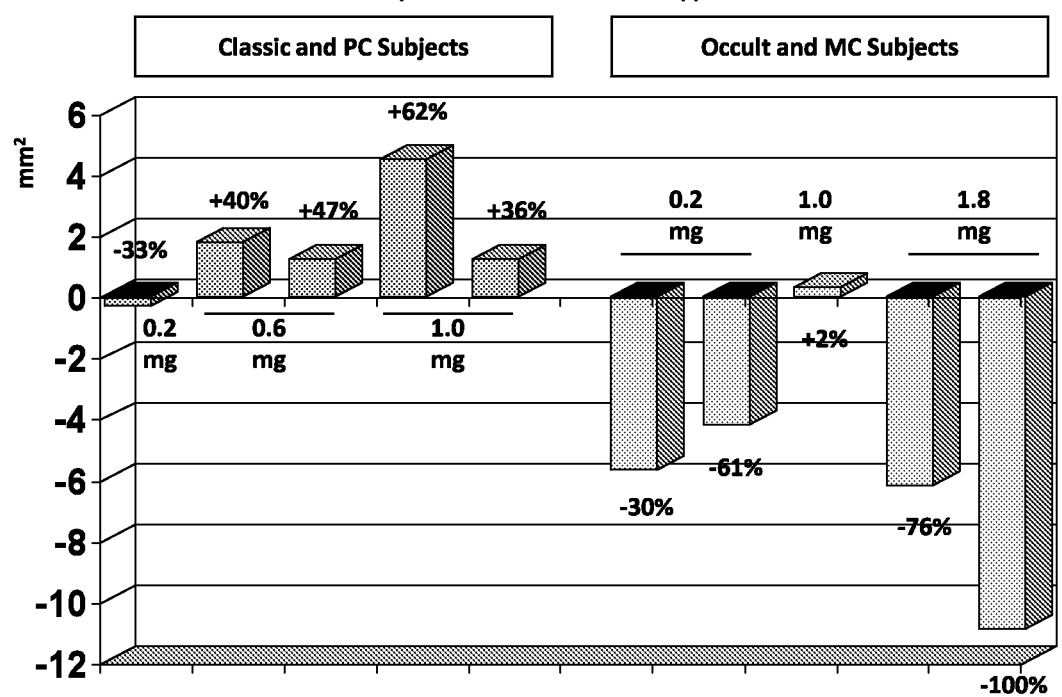
FIG. 1 is a bar graph showing positive and negative changes in CNV lesion area after ISONEP treatment. Extent and direction of change appeared to be correlated with disease subtype, with classic and predominantly classic CNV patients showing minimal decrease but more often an increase in active lesion area. In contrast, patients with occult or minimally classic CNV showed minimal increase but more often a substantial decrease in active lesion area.

Wet AMD is characterized by the pathologic disruption of the retina, which is caused collectively by (i) new blood vessel growth in the choroid layer under the retina; (ii) sub-retinal fibrosis; (iii) inflammation in the retinal area; and (iv) edema caused by new blood vessels that do not form perfectly and may be permeable (leaky).

S1P is believed to be a good target for exudative AMD because it is pro-angiogenic (promotes cell proliferation, migration, tubule formation; potentiates VEGF-induced vascularization by transactivation of VEGF R2) (Visentin, B. et al., (2006) Cancer Cell, 9:225-38; Lee O H (1999) Biochem. and Biophys. Res. Commun. 264:743-50.); it is a mediator of vascular maturation (recruits smooth muscle cells and pericytes; exhibits cross-talk with PDGF receptor) (Liu Y. (2000) J. Clin. Invest., 106:951-61); it is a mediator of vascular permeability (S1P regulates vascular leakage in lung, skin and ocular tissues; deprivation of S1PR2 inhibits vascular leakage in the eye; SPHK inhibitors markedly reduce VEGF-induced vascular leakage in the Miles assay and a rat model of diabetic retinopathy) (Rotstein N P. (2010), J. Lipid Res., doi: 10.1194/jlr.R003442 (epub in advance of print); Wang L. (2009), Microvasc. Res., 77:39-45; Skoura, A. (2007) J. Clin. Invest., 117:2506-16.; Maines, L W. (2006), Invest. Ophthalmol. 47:5022-31; it promotes inflammation (influences expression and release of MCP-1, IL-6, IL-8, COX-2, PAF) (Lai, W Q. (2008), J. Immunol., 181:8010-7; J. Immunol. 180:4323-9); and it is a mediator of fibrosis (transforms fibroblasts into the collagen-producing myofibroblast phenotype; influences the effect of TGF-β; and promotes expression of CTGF and PAI-1) (Caballero S. (2009), Exp. Eye Res., 88:367-77; Swaney, J S. (2008), Exp. Eye Res., 87:367-75; Kono Y. (2007), Amer. J. Resp. Cell & Molecular. Biol., 37:395-404; Muehlich S. (2004), Atherosclerosis, 175:261-8). S1P signaling is present in the posterior segment of the human eye. Primary human RPE cells, retinal and choroidal vascular endothelial cells express S1P receptors, express sphingosine kinases 1 and 2, and contain intracellular pools of S1P. Swaney, J S, 2008.

The predominant market leaders in wet AMD treatment are LUCENTIS® (ranibizumab) or off-label use of AVASTIN® (bevacizumab). Both of these target VEGF, a validated promoter of permeable and leaky blood vessels, and appear to exert much of their beneficial effect via an anti-permeability action that results in resolution of intra- and sub-retinal edema. However, the actual CNV lesion does not typically regress after VEGF inhibitor treatment. In contrast, anti-S1P antibody has been shown in various animal models of disease to reduce blood vessel growth and leakiness and mitigate ocular fibrosis [Grant et al. (2008) Exp. Eye Res. 88:367-77] and to substantially reduce inflammation in the eye [Campochiaro (2009) J. Cell. Physiol 8:192-8]. Thus an anti-S1P antibody has the potential to offer significant advantages over exclusively anti-VEGF approaches to wet AMD treatment. Because of this, anti-S1P antibody may be useful as a combination therapy with VEGF inhibitors (Campochiaro 2009).

Immune-derived moieties against S1P have been developed. An "immune-derived moiety" refers to any polyclonal or monoclonal antibody or antibody fragment, variant, or derivative. An "anti-S1P antibody," an "antibody to S1P" or an "antibody reactive against S1P" refers to any antibody or immune-derived moiety that binds S1P.

The term "antibody" herein is used in the broadest sense and specifically covers monoclonal antibodies (including full length monoclonal antibodies), polyclonal antibodies, multispecific antibodies (e.g., bispecific antibodies), antibody fragments, and binding agents that employ the CDRs (or variant thereof that retain antigen binding activity) of the parent antibody. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile in vitro. "Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments. In a preferred embodiment, the antibody fragment is an antigen-binding antibody fragment.

Such immune-derived moieties, including antibodies and fragments thereof, are described in detail in commonly owned U.S. Pat. No. 7,829,674, commonly owned and co-pending U.S. patent application Ser. No. 12/258,353, now issued as U.S. Pat. No. 7,956,173; commonly owned and co-pending U.S. patent application Ser. No. 12/258,383, now issued as U.S. Pat. No. 8,026,342; and commonly owned and co-pending U.S. patent application Ser. No. 11/925,173, now issued as U.S. Pat. No. 8,614,103, each of which is incorporated herein by reference in their entirety and for all purposes.

Humanized Monoclonal Antibody to S1P-LT1009 (SONEPCIZUMAB)

A humanized monoclonal antibody (rhuMAb S1P) specifically reactive with S1P has been developed by Lpath, Inc. Construction, synthesis, purification, and testing of this antibody, termed LT1009 (Sonepcizumab™), as well other anti-S1P antibodies, antigen-binding fragments, derivatives, and variants, is described in U.S. Pat. No. 7,829,674, commonly owned and co-pending U.S. patent application Ser. No. 12/258,353, now issued as U.S. Pat. No. 7,956,173; commonly owned and co-pending U.S. patent application Ser. No. 12/258,383, now issued as U.S. Pat. No. 8,026,342; and commonly owned and co-pending U.S. patent application Ser. No. 11/925,173, now issued as U.S. Pat. No. 8,614,103. As compared to the murine anti-S1P antibody from which LT1009 was derived, the humanized form exhibits an S1P binding affinity in the picomolar range, as well as and superior stability and in vivo efficacy. Because ISONEP has demonstrated anti-inflammatory, anti-fibrotic and anti-angiogenic activity, the safety and efficacy of ISONEP were evaluated in a Phase I clinical trial in patients with wet AMD.

The therapeutic methods and compositions of the invention act by changing the effective concentration, i.e., the absolute, relative, effective and/or available concentration and/or activities, of certain undesired bioactive lipids, e.g. S1P. Lowering the effective concentration of the bioactive lipid may be said to "neutralize" the target lipid or its undesired effects, including downstream effects. Here, "undesired" refers to a bioactive lipid that is unwanted due to its involvement in a disease process, for example, as a signaling molecule, or to an unwanted amount of a bioactive lipid which contributes to disease when present in excess. It is believed that neutralizing S1P will be efficacious in patients with CNV, wet AMD, pigment epithelial detachment (PED) and other ocular diseases and conditions characterized wholly or in part by inflammation, unwanted angiogenesis and/or fibrosis.

LT1009 (Sonepcizumab) Sequences

As with naturally occurring antibodies, LT1009 includes three complementarity determining regions (each a "CDR") in each of the two light chain polypeptides and each of the two heavy chain polypeptides that comprise each antibody molecule. The amino acid sequences for each of these six CDRs is provided immediately below ("VL" designates the variable region of the immunoglobulin light chain, whereas "VH" designates the variable region of the immunoglobulin heavy chain):

```
LT1009 CDR sequences:
CDR1 VL:
                                        [SEQ ID NO: 1]
ITTTDIDDDMN

CDR2 VL:
                                        [SEQ ID NO: 2]
EGNILRP

CDR3 VL:
                                        [SEQ ID NO: 3]
LQSDNLPFT

CDR1 VH:
                                        [SEQ ID NO: 4]
DHTIH

CDR3 VH:
                                        [SEQ ID NO: 5]
GGFYGSTIWFDF

CDR2 VH:
                                        [SEQ ID NO: 6]
AISPRHDITKYNEMFRG
```

LT1009 Heavy and Light Chain Sequences

Sequences of the LT1009 heavy and light chains (variable domains and full length) are as follows. CDRs are shown in bold.

```
LT1009 HC amino acid sequence of the variable domain [SEQ ID NO: 7]:
evqlvqsgaevkkpgeslkiscqsfgyifidhtihwmrqmpgqglewmgaisprhditkyn emfrgqvtisadkssstaylqwsslkasdtamyfcarggfygstiwfdfwgqgtmvtvss
```

-continued

LT1009 LC amino acid sequence of the variable domain [SEQ ID NO: 8]:
ettvtqspsflsasvgdrvtitcitttdidddmnwfqqepgkapkllisegnilrpgvps rfsssgygtdftltisklqpedfatyyclqsdnlpftfgqgtkleik LT1009 full length heavy chain amino acid sequence (SEQ ID NO: 9)
evqlvqsgaevkkpgeslkiscqsfgyifidhtihwmrqmpgqglewmgaisprhditkynemfrg qvtisadkssstaylqwsslkasdtamyfcarggfygstiwfdfwgqgtmvtvssastkgpsvfpl apsskstsggtaalgclvkdyfpepvtvswnsgaltsgvhtfpavlqssglyslssvvtvpssslg tqtyicnvnhkpsntkvdkrvepkscdkthtcppcpapellggpsvflfppkpkdtlmisrtpevt cvvvdvshedpevkfnwyvdgvevhnaktkpreeqynstyrvvsvltvlhqdwlngkeykckvsnk alpapiektiskakgqprepqvytlppsreemtknqvsltclvkgfypsdiavewesngqpennyk ttppvldsdgsfflyskltvdksrwqqgnvfscsvmhealhnhytqkslslspgk LT1009 full length light chain amino acid sequence [SEQ ID NO 10]:
ettvtqspsflsasvgdrvtitcitttdidddmnwfqqepgkapkllisegnilrpgvpsrfsssg ygtdftltisklqpedfatyyclqsdnlpftfgqgtkleikrtvaapsvfifppsdeqlksgtasv vcllnnfypreakvqwkvdnalqsgnsqesvteqdskdstyslsstltlskadyekhkvyacevth qglsspvtksfnrgec The C-Terminal Lysine on the LT1009 Heavy Chain May Not Be Present On the Mature Heavy Chain Protein.

While the nucleotide and amino acid sequences for LT1009 heavy chain reveal a lysine as the last (most C-terminal) amino acid residue of the protein, LT1009 when expressed, for example, in CHO cell clone LH1 275, does not contain the C-terminal lysine. This has been demonstrated by peptide mapping and, while not wishing to be bound by theory, is believed to result from posttranslational modification of the protein in mammalian systems. Again not wishing to be bound by theory, it is believed that in other expression systems, particularly nonmammalian systems, the C-terminal lysine is present on the mature LT1009 heavy chain.

The LT1009 full length heavy chain amino acid sequence as expressed in CHO cells (i.e., without the C-terminal lysine) is shown below. CDRs are in bold.

[SEQ ID NO 11]:
evqlvqsgaevkkpgeslkiscqsfgyifidhtihwmrqmpgqglewm gaisprhditkynemfrgqvtisadkssstaylqwsslkasdtamyfc arggfygstiwfdfwgqgtmvtvssastkgpsvfplapsskstsggta algclvkdyfpepvtvswnsgaltsgvhtfpavlqssglyslssvvtv pssslgtqtyicnvnhkpsntkvdkrvepkscdkthtcppcpapellg gpsvflfppkpkdtlmisrtpevtcvvvdvshedpevkfnwyvdgvev hnaktkpreeqynstyrvvsvltvlhqdwlngkeykckvsnkalpapi ektiskakgqprepqvytlppsreemtknqvsltclvkgfypsdiave wesngqpennykttppvldsdgsfflyskltvdksrwqqgnvfscsvm healhnhytqkslslspg Ocular Formulations of SONEPCIZUMAB Therapeutic formulations of anti-S1P antibody, S1P-binding antibody fragment, and the like are prepared for storage and subsequent administration by mixing a suitably purified preparation of the active ingredient (e.g., from about 10 mg/mL to about 50 mg/mL of purified LT1009) with one or more physiologically acceptable carriers, excipients, or stabilizers (see, e.g., Remington's Pharmaceutical Sciences 16th edition, Osol, A. Ed. (1980)), preferably in the form of an aqueous solution. Preferred carriers, as well as other excipients or stabilizers included in a given formulation, are those that are pharmaceutically or veterinarily acceptable, depending upon whether the subject to treated is a human or a non-human mammal. Such materials should also be physiologically compatible, i.e., nontoxic to subjects at the dosages and concentrations employed.

Pharmaceutically acceptable carriers preferably comprise a buffered solution having a pH that is between about pH 5 and about pH 8, optionally between about pH 6 and about pH 7. Suitable buffers include histidine, phosphate, citrate, and other organic acids. In a preferred embodiment, the buffer has a pH of about 6.1. In another preferred embodiment, the buffer is a histidine, citrate or phosphate buffer having a pH of about 6.1.

Therapeutic aqueous formulations according to the invention preferably include salt-forming counter-ions such as sodium. In several preferred embodiments, sodium chloride is included in the composition at a concentration ranging from about 50 mM to about 450 mM. Particularly preferred sodium chloride concentrations range from about 100 mM (0.1M) to about 250 mM (0.25M), with sodium chloride concentrations of about 148 mM (0.148M) being especially preferred.

Certain therapeutic aqueous formulations also preferably include a non-ionic surfactant. Examples of such compounds include TWEEN™, PLURONICS™, and polyethylene glycol (PEG). A particularly preferred non-ionic surfactant is polysorbate-80, also known as TWEEN™ 80. With respect to polysorbate-80, it is preferred that it be used in a concentration of less than about 200 parts per million (ppm) (0.02% by weight) although compositions containing 500 ppm or more (0.05% by weight) can be prepared.

Other materials can also optionally be included in a composition according to the invention, such as antioxidants (including ascorbic acid and methionine); preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; and metal complexes (e.g., Zn-protein complexes).

The formulations to be used for in vivo administration must be sterile. This is readily accomplished, for instance, by filtration through sterile filtration membranes.

A preferred ocular formulation of the anti-S1P antibody SONEPCIZUMAB was developed to be stable and active for intravitreal injection. This formulation, known as ISONEP, is SONEPCIZUMAB (typically 10 mg/mL or 20 mg/mL) in 24 mM sodium phosphate, 148 mM NaCl, 0.02% Polysorbate 80, pH 6.6 or 6.1.

A second ocular formulation has also been developed. This formulation is SONEPCIZUMAB in 50 mM histidine, 100 mM NaCl, 2% trehalose, and 0.005% Polysorbate 80, pH 6.0.

Additional anti-S1P antibody formulations are described in commonly owned and co-pending U.S. patent application Ser. No. 12/418,597, the contents of which are incorporated by reference herein in their entirety and for all purposes.

The formulations of the invention of the invention are typically packaged and stored in labeled containers, such as bottles, vials, and syringes formed from a variety of materials such as glass or plastic. A container generally also includes a sterile access port. The label on, or associated with, the container indicates that how to use formulation for treating the condition of choice. Such containers may be packaged with other containers, which may, for example, contain a pharmaceutically-acceptable buffer, diluent, or solution for resuspending a dry formulatiom, such as phosphate-buffered saline, Ringer's solution, or dextrose solution. Other items that may also be present in such packaging may further include materials desirable from a commercial and user standpoint, including other buffers, diluents, filters, needles, syringes, package inserts with instructions for use, and the like.

Routes of Antibody Administration

Exemplary routes of administration of an antibody in methods according to the invention include systemic administration, parenteral administration (e.g., via injection via an intravenous, intramuscular, or subcutaneous route), transdermal, intradermal or transmucosal delivery, ocular administration, mucosal or topical administration or by inhalation. Ocular administration includes intraocular or periocular administration, and may be, e.g., by means of implants, administration devices, or intraocular injection, including intravitreal injection.

The role of bioactive lipids, particularly S1P, in disease, including ocular disease, and anti-S1P antibodies, are described in detail in commonly owned U.S. Pat. No. 7,829,674, U.S. patent application Ser. No. 12/258,353, now issued as U.S. Pat. No. 7,956,173; commonly owned and co-pending U.S. patent application Ser. No. 12/258,383, now issued as U.S. Pat. No. 8,026,342; and commonly owned and co-pending U.S. patent application Ser. No. 11/925,173, now issued as U.S. Pat. No. 8,614,103. Anti-S1P antibody formulations are described in commonly owned and co-pending U.S. patent application Ser. No. 12/418,597. This application incorporates by reference for all purposes all of the aforementioned applications, each in its entirety.

EXAMPLES

The invention will be further described by reference to the following detailed Examples, which are in no way to be considered to limit the scope of the invention.

Example 1

Phase I Clinical Trial of Anti-S1P mAb (iSONEP) in Patients with Exudative AMD

Subjects with all sub-types of CNV secondary to AMD were enrolled in a Prospective Open-Label Dose-Escalating Multi-Center Phase I clinical trial to evaluate the safety, maximum tolerated dose (MTD) and preliminary activity of iSONEP in subjects with exudative AMD.

The primary objectives of the trial were safety, tolerability and establishment of MTD and dose-limiting toxicity (DLT). The secondary objectives were to characterize pharmacokinetics (PK), evaluate immunogenicity, investigate signs of biologic activity [CNV lesion area by fluorescein angiography (FA) and retinal thickness by optical coherence tomography (OCT) using the STRATUS imaging device and software (Zeiss). OCT is a non-invasive, non-contact method giving a cross sectional image of the living retina and its substructures in real time]. Visual acuity was also evaluated, measured as best corrected visual acuity using the Early Treatment Diabetic Retinopathy Study chart (BCVA ETDRS).

The study design was as follows: Fifteen subjects, three per dose group, with CNV secondary to AMD, were given a single intravitreous injection of ISONEP at a dose of 0.2, 0.6, 1.0, 1.4 or 1.8 mg/eye in one eye.

Ocular study evaluations were designed as follows: A single dose of ISONEP was given at day 1. Ophthalmic examination was done at screening, day 1 (pre and post dose), days 3, 8, 15, 30, 45 and 90, and months 6, 9 and 12. Fluorescein angiography (FA) and fundus photography were done at screening, days 15, 30, 45 and 90, and month 12. OCT was done at screen, days 8, 15, 30, 45 and 90 and month 12.

Key inclusion criteria were as follows: males and females at least 50 years of age; BCVA ETDRS between 20-57 letters in study eye (equivalent to 20/70 to 20/400 on the Snellen chart); CNV secondary to AMD with leakage on FA (all subtypes allowed and subfoveal, juxtafoveal, extrafoveal locations allowed) and intraretinal or subretinal fluid on OCT; eyes with subfoveal fibrosis were allowed; FA and OCT interpretation at entry based on investigator assessment; investigator not permitted to treat eye with another therapy before day 30.

Key exclusion criteria were as follows: Previous anti-VEGF treatment<6 weeks prior to day 1; triamcinolone<6 months prior to day 1; photodynamic therapy (PDT)<12 weeks prior to day 1; investigational agents<6 weeks prior to day 1. Other exclusion criteria were intraocular or general surgery, including cataract surgery, within two months of day 1; history of uveitis in either eye, ocular or periocular infection within 4 weeks prior to day 1; intraocular pressure>21 mmHg in subjects with glaucoma being treated with >2 ocular hypotensive agents; previous pars plana vitrectomy or trabeculectomy in study eye; history of anterior vitrectomy.

The fifteen patients had baseline characteristics as follows (unverified data):
Age: mean 75.8 yr; range 58-91.
Gender: 9 male, 6 female.
Disease duration in months*: mean 24.3, range 1-125.
  *month of dx unknown, assumes full year for subject #11
Number of prior treatments: mean 8, range 0-24.

Lesion type:
  Pure classic: 5 (33%)
  Pure occult: 3 (20%)
  Minimally classic: 2 (13%)
  Predominantly classic: 2 (13%)
  Disciform scar: 3 (20%).
Disease characteristics:
  Mean area of CNV (mm$^2$): mean 6.56, range 0.00-18.99.
  Mean central retinal thickness (μm)**: mean 282; range 142-540
  **mean of measurements taken by two readers
  BCVA ETDRS letters (Snellen): mean 41.7 (~20/160); range 30-55.

Example 2

Safety Results of Phase I Trial

ISONEP was found to be well tolerated at all doses. No dose-limiting toxicity (DLT) was observed at any dose and the MTD was not reached. No significant adverse effects related to ISONEP were observed. Five adverse effects were potentially related to ISONEP: one occurrence of conjunctival hemorrhage, two instances of eye pain, and a 3 ms increase in QTcB interval and bundle branch block (observations on ECG) in the same subject, who had been treated with ISONEP at 0.2 mg and had a prior history of arrhythmia. All adverse effects resolved without sequelae. Thus iSONEP met its primary endpoint of being well tolerated in all 15 patients at dose-levels ranging from 0.2 mg. to 1.8 mg. per intravitreal injection (three patients per dose level). No drug-related serious adverse events were reported in any of the patients.

Interestingly, preliminary indications of biologic activity were seen in this Phase I trial. Five of the fifteen subjects on study were not evaluable for biologic activity, either because they were found to have no active CNV at screening (3 subjects), or because they were treated prematurely with AVASTIN® (bevacizumab), a violation of study protocol (2 subjects). These subjects were included in the safety study results described above, but not in the preliminary analysis of biologic activity described in examples below. Thus iSONEP also succeeded in meeting a key secondary endpoint in that a positive biological effect was observed in an encouraging number of patients.

Example 3

Reduction in Active CNV Lesion Area After Single Treatment

CNV lesion area was determined by fluorescence angiography (FA), with reading of images performed at the Digital Angiography Reading Center (DARC), New York, N.Y., a fully digital reading center for FA images. Each image was evaluated by two readers.

A regression in CNV was observed after treatment with ISONEP. CNV is the underlying cause of the disease that eventually leads to degeneration of the macula, the area of the retina responsible for central vision. Of ten patients, three experienced a reduction in lesion area exceeding 5 mm·sup·2 and two experienced a reduction of greater than 75%—all after a single dose of ISONEP. This type of clinical benefit is not typical, as the published data [Heier J S et al. (2006) Ophthalmology 113:642e1-642e4] suggest that, even with repeated LUCENTIS® (ranibizumab) dosing, the total physical size of CNV lesion(s) does not show much reduction. LUCENTIS® (ranibizumab) and AVASTIN® (bevacizumab) target the protein VEGF, a validated promoter of permeable and leaky blood vessels, and are believed to have an anti-permeability action that results in resolution of intra and sub-retinal edema. However, the actual CNV lesion does not typically regress as it was shown to do with iSONEP treatment. In contrast, iSONEP has been shown in various animal models of disease not only to reduce blood-vessel growth and leakiness, but to significantly mitigate ocular fibrosis (Grant et al, Experimental Eye Research, August 2008) and to substantially reduce inflammation in the eye (Campochiaro et al., Journal of Cellular Physiology, October 2008). The fact that these biological effects are non-overlapping vis-a-vis those of LUCENTIS® (ranibizumab) and AVASTIN® (bevacizumab) is significant. As such, iSONEP may offer specific advantages over exclusively anti-VEGF approaches to treatment of wet AMD. iSONEP may also act synergistically with anti-VEGF treatments as a combination therapy to address the complex processes and multiple steps that ultimately lead to vision loss for wet-AMD patients.

Example 4

Change in Central Retinal Lesion Thickness After Single Treatment

Measurement of the thickness of the central retinal lesion is an indicator of extent and progression of CNV disease. Central retinal lesion thickness was measured by optical coherence tomography (OCT) and all OCT images were captured using the Zeiss STRATUS imaging device and software. OCT is a non-invasive, non-contact method giving a cross sectional image of the living retina and its substructures in real time. OCT images were sent to an independent reading center [Digital OCT Reading Center (DOCTR), Cleveland, Ohio]. At study sites having a spectral domain OCT system (SDOCT), a SDOCT scan of the central macula (using the standard protocol for the system) was also performed.

The thickness of the central retinal lesion was measured at day 15 and day 30 after single-dose ISONEP treatment and compared to the baseline thickness at time of screening. Preliminary results indicate that at day 15, eight of the ten evaluable patients showed a decrease in central retinal lesion thickness (CRLT); of these, 3 of 5 patients with classic CNV showed a decrease in CRLT and 5 of 5 patients with occult CNV showed a decrease in CRLT. At day 30, 5 of 8 evaluable patients (two subjects did not have OCT at day 30) showed a decrease in CRLT. Of these, 3 of 5 patients with classic CNV and 2 of 3 patients with occult CNV showed a decrease in CRLT.

Example 5

Subgroup Analysis

As can be seen in FIG. 1, the reduction in CNV lesion area (Example 3) appeared to be correlated with disease type. Four of the five patients with a component of occult disease (either occult or minimally classic lesion type) showed a decrease in lesion size. These decreases ranged from 30% to 100% decrease in size. In contrast, four of the five patients with classic or predominantly classic disease showed an increase in lesion size, with increases ranging from 36% to 62%. Thus patients with a component of occult disease exhibited a strong positive biologic effect following a single injection of ISONEP.

In addition, patients with a component of occult disease also showed a stronger biologic effect on central retinal lesion thickness (CRLT) after a single injection of ISONEP, as described in the previous example. Table 1 shows an analysis of biologic activity (lesion size and visual acuity) in the five evaluable patients with a component of occult disease (pure occult or minimally classic).

TABLE 1

Subgroup Analysis- Evaluable Subjects with Pure Occult ("Occult") or Minimally Classic ("MC") Disease

| Pt. # Dose CNV Type | Dx Date # Prior Treatments | Evaluation Days | Lesion area by FA (mm²) | Visual Acuity Letter Score | Days to anti-VEGF rescue treatment |
|---|---|---|---|---|---|
| 1 0.2 mg Occult | 4/2005 23 + PDT | Screening Day 30 | 18.99 13.25 | 35 50 | ~60 days |
| 2 0.2 mg Occult | 6/2008 2 + PDT | Screening Day 30 | 6.90 2.70 | 55 38 | >15 months |
| 9 1.0 mg Occult | 12/2008 None | Screening Day 15 Day 30 | 15.18 15.52 | 42 41 | ~75 days |
| 14 1.8 mg MC | 1/2005 9 | Screening Day 15* Day 30 | 8.18 1.99 | 39 42 | ~30 days |
| 15 1.8 mg MC | 7/2007 16 + triple therapy | Screening Day 30 Day 54 | 10.95 0 0 | 30 35 32 | >9 months |

It can be seen that the five patients with a component of occult disease generally showed reduction in lesion size by FA, reduction in retinal thickness, and most had no loss of visual acuity. Notably, these patients did not need "rescue" treatment with a VEGF inhibitor (the current standard of care) for at least 30 days, with two patients currently at >9 months and >15 months with no rescue treatment.

In subject 15, with minimally classic disease (i.e., having a component of occult disease), the lesion regressed completely (from 10.95 mm² to zero) by day 15 and remained at zero for the remainder of the study (day 45).

While the ability to draw preliminary conclusions from this Phase I study is limited by the small sample size and lack of a control group (typical of Phase I which is intended to be only a safety study and not an analysis of drug activity or effect), it appears that there may be clinically meaningful biologic activity after ISONEP treatment, at least in some patients. In particular, patients having some component of occult CNV (i.e., having occult or minimally classic CNV) appear to show beneficial effect of treatment. Unexpectedly, of the five patients that showed the strongest biological effect, all five had a component of occult-type CNV (either pure occult CNV or "minimally classic" CNV). Further, these five patients were the only ones in the Phase I study that were diagnosed with occult disease. In other words, all of the patients with a component of occult CNV exhibited a strong positive biological effect during the 30-45 days following a single injection of iSONEP.

Example 6

Visual Acuity After Single Treatment

Visual acuity is measured in terms of the number of letters that can be read on the ETDRS chart. While these results are considered preliminary due to the small number of patients in this study and the variability seen from day to day in visual acuity, some trends were seen. Table 2 summarizes the visual acuity data at day 30. Some patients were treated with VEGF inhibitors (LUCENTIS® (ranibizumab) or AVASTIN® (bevacizumab)), which was permitted as early as day 30 of the ISONEP trial. The effect of ISONEP (and where treated, VEGF inhibitor) on visual acuity is shown in Table 2.

TABLE 2

Effects on Visual Acuity at Day 30

| Pt # | CNV subtype | Letters Gained or Lost | Anti-VEGF effect |
|---|---|---|---|
| 1 | Occult | +15 | Not known |
| 2 | Occult | -17 | Not yet retreated |
| 3 | Classic | -3 | 0 |
| 5 | Classic | -6 | -7 |
| 6 | Classic | -7 | +1 |
| 7 | Classic | +15 | -16 |
| 8 | Classic | +1 | +2 |
| 9 | Occult | -1 | Not known |
| 14 | Classic & Occult | +3 | +1 |
| 15 | Classic & Occult | +5 | Not yet retreated |
|  | AVERAGE | +1 | -3 |

In general, patients experienced stable visual acuity or slight improvement in acuity after ISONEP treatment. This compares favorably to the outcome after subsequent VEGF inhibitor treatments, if indeed such treatment was needed.

Example 7

Resolution of Retinal Pigment Epithelial Detachment (PED) After Single Treatment Retinal pigmented epithelium (RPE) detachment, also referred to as pigment epithelial detachment (PED), is a potentially serious condition that is often a part of the pathology of wet AMD and is often not responsive to conventional therapy. Two patients were diagnosed with PED in this Phase I trial, and both experienced complete or near-complete resolution of the detachment after a single dose of ISONEP. Neither LUCENTIS® (ranibizumab) nor AVASTIN® (bevacizumab) typically produce this type of clinical benefit with a single dose.

Of ten evaluable patients, two were noted to have a PED by optical coherence tomography (OCT). One patient (#2), a 65 yo female with PED and occult CNV, had two prior AVASTIN® (bevacizumab) treatments and laser treatment. Following a single intravitreal injection of ISONEP (0.2 mg), this subject had complete resolution of active CNV lesion and by day 45 there was no evidence of PED (as can be seen in FIG. 2A, described below). VA was stable with a loss of 17 letters. Well over a year after the single treatment with ISONEP, the patient has not required anti-VEGF treatment. The other patient (#9), a 76 yo female with PED and juxtafoveal occult CNV, had no prior anti-VEGF treatment. By day 45 following a single intravitreal injection of 1.0 mg ISONEP, there was complete resolution of the PED and CNV lesion activity, and VA was stable. This subject received treatment with AVASTIN® (bevacizumab) on day 105.

Though limited in number, subjects with a PED at study entry showed remarkable and unexpected improvement with a single intravitreal injection of ISONEP (0.2 or 1.0 mg dose).

Example 8

Resolution of Subretinal and Intraretinal Edema

In CNV lesions, fluid can accumulate under the retina (subretinal edema) or within the retina (intraretinal edema), distorting the retinal architecture. After a single treatment with ISONEP, a reduction in intraretinal and/or subretinal edema may be seen. Examples of such edema and the reduction of it after ISONEP treatment are shown in FIGS. 2 and 3. For example, FIG. 2A shows a series of fundus (left portion of each image—gray background) and OCT images (right side of each image—black background) from patient 2, an individual with occult CNV who was dosed with 0.2 mg of ISONEP. The subretinal edema and associated deformation of the retinal architecture can be seen in the OCT images to diminish over time after the ISONEP treatment. A pigment epithelial detachment in this patient also resolved. The epithelium is the bright white line that appears as an inverted bowl shape in the screening OCT photograph (due to subretinal edema) and flattens out by day 45.

FIG. 2B shows a series of FA images over time, also from patient 2. The top row of images is from screening prior to ISONEP treatment, and subsequent rows are from days 15, 30 and 45 after treatment. Each individual image from left to right represents individual time points after dye (fluorescein) injection. By day 45 the lesion was determined to have regressed completely. This resolution can be seen by comparing the images in the top and bottom rows.

FIG. 3 shows a series of OCT images from patient 15, an individual with minimally classic CNV who was dosed with 1.8 mg ISONEP. This patient had intraretinal edema (dark bubbles near center of each image) that can be seen to resolve completely over time.

Example 9

PEDIGREE, a Ph1b/2a Study in Patients with Pigment Epithelial Detachment (PED)

Based on the results of the Phase 1 trial described in the previous examples, a Phase 1b/2a clinical trial is about to begin. This trial, known as PEDigree, may generally be conducted as follows. Thirty two subjects with PED secondary to wet AMD or polypoidal choroidal vasculopathy (PCV) will be enrolled. The primary objective of the study is to evaluate safety and tolerability following one, two or three intravitreous injections of iSONEP and to investigate the ability of iSONEP to induce regression of persistent PED in subjects with exudative AMD or in subjects with PCV despite previous treatment with an anti-VEGF agent (either (LUCENTIS® (ranibizumab)) or Avastin (AVASTIN® (bevacizumab)).

Inclusion criteria are: subjects who have had multiple anti-VEGF treatments, yet their PED persists (≤25% resolved), and who have an EDTRS BCVA score of ≥24 and TBD (approximately 20/320 and 20/50 on the Snellen scale) and ETDRS visual acuity of 20/400 or better in the fellow eye. Also, patients must exhibit SDOCT in the 1 mm central macular subfield on the retinal map analysis of ≥300 µm as determined by the reading center at screening.

Excluded are subjects who have subfoveal fibrosis or atrophy. The enrollment of 32 subjects will be based on a 3:1 stratification to represent the incidence of AMD and PCV in the general population; 24 AMD subjects and 8 PCV subjects will be randomized following a ratio of 1:1 to each arm. Twelve AMD and four PCV subjects will be randomized to 0.5 mg/eye and another group of 12 AMD and 4 PCV subjects will receive 2.0 mg/eye Dosing with iSONEP will take place on Day 1 with the potential of a second injection at Day 30 and a third injection at Day 60 if there is evidence of residual PED. iSONEP is administered by intravitreal injection in 50 mM histidine, 100 mM NaCl, 2% trehalose, 0.005% polysorbate 80, pH 6.0.

Additional endpoints include: determining changes in sub-retina I and intraretinal fluid, in retinal thickness and in size and height of PED compared with baseline at Days 30, 45, 60 and 90 as determined by SDOCT; evaluating changes in CNV lesion area from baseline as determined by FA; determining the time course to regression of PED; proportion of subjects with complete resolution of PED following a single intravitreous injection of iSONEP; assessing the proportion of subjects requiring a second and a third intravitreous injection to achieve complete resolution of PED; examining changes in visual acuity; proportion of eyes gaining greater than or equal to 0, 5, 10 and 15 letters on the ETDRS chart; determining the proportion of subjects with an improvement from baseline in the Visual Function Questionnaire (VFQ-25) overall composite score (near and distance activities) to Day 60, Month 4 and Month 8; determining the time to re-treatment with anti-VEGF therapy; evaluating the immunogenicity (antibody response) of iSONEP following multiple intravitreous injections; and characterizing the systemic pharmacokinetic profile of iSONEP.

Patients are monitored for PED collapse by SDOCT, and if the PED is not fully collapsed (resolved), an additional dose of iSONEP is given by intravitreal injection on days 30 and 60. The endpoints of the trial are: safety of multiple injections, percentage of subject with collapsed PED, reduction in height and area of PED, durability (time course) of PED changes, changes in sub-retinal and intra-retinal fluid, change in CNV lesion area, change in best corrected visual acuity (BCVA) and time to re-treatment.

Example 10

NEXUS: A Phase 2a Study in Wet-AMD Patients Without PED

Based on the results of the Phase 1 trial described above, a larger phase 2a study of iSONEP in patients with wet (exudative) AMD will be conducted, generally as follows. This trial, known as NEXUS, will enroll 160 wet AMD patients who do not have PED.

Inclusion criteria are: Active subfoveal CNV secondary to AMD (leakage on FA) as determined by reading center at screening; SDOCT in the 1 mm central macular subfield on the retinal map analysis of ≥300 µm as determined by the reading center at screening; EDTRS BCVA score of ≥24 and TBD (approximately 20/320 and 20/50 on the Snellen scale); ETDRS visual acuity of 20/400 or better in the fellow eye.

Excluded are subjects that have subfoveal fibrosis or atrophy, or who have PED.

Five treatment groups will be randomly assigned. Two groups will constitute the iSONEP monotherapy arm, two groups will make up the adjunctive therapy arm and one group will be the active control arm. All randomized subjects will receive monthly intravitreous injections for 4 consecutive months and will be followed up for a period of 6 months from their last study treatment.

Group 1: iSONEP 2.0 mg/Sham Lucentis (n=20)
Group 2: iSONEP 4.0 mg/Sham Lucentis (n=20)
Group 3: iSONEP 0.5 mg/Lucentis (n=40)
Group 4: iSONEP 4.0 mg/Lucentis (n=40)
Group 5: Lucentis/Sham iSONEP (n=40)

Subjects in Group 1 will receive an intravitreous injection containing 2.0 mg of iSONEP in 50 µL (10 mg/mL) and a sham injection. Group 2 subjects will receive an intravitreous injection containing 4.0 mg of iSONEP in 100 µL (40 mg/mL) and a sham injection. iSONEP is formulated in 50 mM histidine, 100 mM NaCl, 2% trehalose, 0.005% polysorbate 80, pH 6.0. Group 3 subjects will receive intravitreous injections containing 0.5 mg of iSONEP in 50 μL (10 mg/mL) and 0.5 mg of Lucentis in 50 μL (10 mg/mL); both injections will be given at a 1-hour interval. Group 4 subjects will receive intravitreous injections containing 4.0 mg of iSONEP in 100 μL (40 mg/mL) and 0.5 mg of Lucentis in 50 μL (10 mg/mL); both injections will be given at a 1-hour interval. Group 5 subjects will receive an intravitreous injection containing 0.5 mg of Lucentis in 50 μL (10 mg/mL) and a sham injection.

Methodology includes use of: Best-Corrected Visual Acuity (BCVA) using the 4-meter ETDRS protocol, at all study visits; slit lamp biomicroscopy examination and indirect ophthalmoscopy will be assessed at all study visits; IOP will be measured by applanation tonometry at all study visits. IOP will also be measured at each treatment visit prior to each injection, 30 minutes to one hour post the first injection and 30 minutes to one hour post the second injection. Prior to the second injection, the IOP increase must be less than 10 mmHg or a maximum of 30 mmHg.; fluorescein angiography (FA) and fundus photography will be taken at screening, Days 1 (Baseline), 30, 60 and 90 and Months 4 through 9; spectral Domain Optical Coherence Tomography (SDOCT): SDOCT will be obtained at screening, Days 1 (baseline), 30, 60 and 90 and Months 4 through 9. Only the Cirrus SDOCT will be used in this study.

The primary endpoints include: safety and tolerability following four monthly intravitreous injections of iSONEP given alone or with Lucentis and mean change in the best-corrected visual acuity score measured by ETDRS from Day 1 (baseline) to Week 16 of iSONEP alone or given with Lucentis compared to Lucentis alone. Secondary endpoints include; mean change in visual acuity from baseline to Week 16; proportion of eyes gaining greater than or equal to 0, 5, 10 and 15 letters on the ETDRS chart; number of subjects with visual acuity of 20/50 or better; mean change in central subfield retinal thickness from baseline to Week 16, by SDOCT; changes in CNV lesion area from baseline to Week 16 as determined by FA; and number of subjects with adverse events.

---

What is claimed is:

1. A method selected from the group consisting of:
   (a) a method of treating a subject having an occult or minimally classic choroidal neovascularization lesion, comprising administering an anti-sphingosine-1-phosphate (S1P) antibody or S1P-binding antibody fragment in an amount sufficient to reduce the size of the choroidal neovascularization lesion;
   (b) a method of treating retinal pigment epithelial detachment, comprising administering to an affected eye of a subject having or suspected of having retinal pigment epithelial detachment, an anti-S1P antibody or S1P-binding antibody fragment in an amount sufficient to stabilize or decrease the retinal pigment epithelial detachment;
   (c) a method of reducing central retinal thickness in an eye of a subject having an occult or minimally classic choroidal neovascularization lesion, comprising administering an anti-S1P antibody or S1P-binding antibody fragment in an amount sufficient to cause a reduction in central retinal thickness of the eye; and
   (d) a method for preserving or improving visual acuity in a patient having or suspected of having an occult or minimally classic choroidal neovascularization lesion, comprising administering an anti-S1P antibody or S1P-binding antibody fragment in an amount sufficient to preserve or improve visual acuity.

2. A method according to claim 1 wherein the anti-S1P antibody or S1P-binding antibody fragment is administered via ocular administration, optionally via intravitreal injection.

3. A method according to claim 1 wherein the subject has or is suspected of having age-related macular degeneration.

4. A method according to claim 3 wherein the age-related macular degeneration is exudative age-related macular degeneration.

5. A method according to claim 1(b) wherein said treating results in a resolution of pigment epithelial detachment.

6. A method according to claim 1(b) wherein the retinal pigment epithelial detachment stems from age-related macular degeneration.

7. A method according to claim 6 wherein the age-related macular degeneration is exudative age-related macular degeneration.

8. A method according to claim 1(c) wherein the choroidal neovascularization is occult and/or minimally classic choroidal neovascularization.

9. A method of treating an ocular disease or condition, comprising administering an effective amount of an ocular pharmaceutical formulation comprising an anti-sphingosine-1-phosphate (S1P) antibody or S1P-binding antibody fragment, a buffer, sodium chloride, and an ionic surfactant, wherein the ocular pharmaceutical formulation has a pH within the range of about pH 6 to about pH 7, to an eye of a subject known to have or suspected of having an ocular disease or condition correlated with S1P, wherein the ocular disease or condition is occult or minimally classic CNV, retinal pigment epithelial detachment, or thickening of the retina or loss of visual acuity associated with occult or minimally classic CNV.

10. A method according to claim 9, wherein the formulation is administered via ocular administration, optionally via intravitreal injection.

11. A method according to claim 10 wherein the age-related macular degeneration is exudative age-related macular degeneration.

* * * * *

SEQUENCE LISTING

<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 1

Ile Thr Thr Thr Asp Ile Asp Asp Asp Met Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 2

Glu Gly Asn Ile Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Humanized antibody sequence

<400> SEQUENCE: 3

Leu Gln Ser Asp Asn Leu Pro Phe Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Humanized antibody sequence

<400> SEQUENCE: 4

Asp His Thr Ile His
1               5

```
<210> SEQ ID NO 5
<211> LENGTH: 12
<212> TYPE: PRT
<213> ORGANISM: Artificial Sequence
<220> FEATURE:
<223> OTHER INFORMATION: Humanized antibody sequence

<400> SEQUENCE: 5

Gly Gly Phe Tyr Gly Ser Thr Ile Trp Phe Asp Phe
1               5                  10

<210> SEQ ID NO 6
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 6

Ala Ile Ser Pro Arg His Asp Ile Thr Lys Tyr Asn Glu Met Phe Arg
1               5                   10                  15

Gly

<210> SEQ ID NO 7
<211> LENGTH: 121
<212> TYPE: PRT
<213> ORGANISM: Artificial Sequence
<220> FEATURE:
<223> OTHER INFORMATION: Humanized antibody sequence

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 8

Glu Thr Thr Val Thr Gln Ser Pro Ser Phe Leu Ser Ala Ser Val Gly
1               5                   10                  15

Asp Arg Val Thr Ile Thr Cys Ile Thr Thr Thr Asp Ile Asp Asp Asp
            20                  25                  30
```

```
Met Asn Trp Phe Gln Gln Glu Pro Gly Lys Ala Pro Lys Leu Leu Ile
            35                  40                  45

Ser Glu Gly Asn Ile Leu Arg Pro Gly Val Pro Ser Arg Phe Ser Ser
 50                  55                  60

Ser Gly Tyr Gly Thr Asp Phe Thr Leu Thr Ile Ser Lys Leu Gln Pro
 65                  70                  75                  80

Glu Asp Phe Ala Thr Tyr Tyr Cys Leu Gln Ser Asp Asn Leu Pro Phe
                 85                  90                  95

Thr Phe Gly Gln Gly Thr Lys Leu Glu Ile Lys
            100                 105

<210> SEQ ID NO 9
<211> LENGTH: 451
<212> TYPE: PRT
<213> ORGANISM: Artificial Sequence
<220> FEATURE:
<223> OTHER INFORMATION: Humanized antibody sequence

<400> SEQUENCE: 9

Glu Val Gln Leu Val Gln Ser Gly Ala Glu Val Lys Lys Pro Gly Glu
 1               5                  10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
            35                  40                  45

Gly Ala Ile Ser Pro Arg His Asp Ile Thr Lys Tyr Asn Glu Met Phe
 50                  55                  60

Arg Gly Gln Val Thr Ile Ser Ala Asp Lys Ser Ser Thr Ala Tyr
 65                  70                  75                  80

Leu Gln Trp Ser Ser Leu Lys Ala Ser Asp Thr Ala Met Tyr Phe Cys
                 85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
 130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
 210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Humanized antibody sequence

<400> SEQUENCE: 10

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 450
<212> TYPE: PRT
<213> ORGANISM: Artificial Sequence
<220> FEATURE:
<223> OTHER INFORMATION: Humanized antibody sequence

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

-continued

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```